(12) United States Patent
Hemminger et al.

(10) Patent No.: US 11,738,106 B2
(45) Date of Patent: Aug. 29, 2023

(54) PREFILLED SYRINGE AND METHOD OF PREPARING A PREFILLED SYRINGE

(71) Applicants: F. HOFFMANN-LA ROCHE AG, Basel (CH); GENENTECH, INC., South San Francisco, CA (US)

(72) Inventors: Markus Hemminger, Basel (CH); Ulla Grauschopf, Basel (CH); Frank Bamberg, Basel (CH); Mayumi Bowen, South San Francisco, CA (US); Robert Müller, Basel (CH); Flora Felsovalyi, Basel (CH); Denny Christensen, South San Francisco, CA (US)

(73) Assignees: F. HOFFMANN-LA ROCHE AG, Basel (CH); GENENTECH, INC., South San Francisco, CA (US)

( * ) Notice: Subject to any disclaimer, the term of this patent is extended or adjusted under 35 U.S.C. 154(b) by 165 days.

(21) Appl. No.: 16/651,444

(22) PCT Filed: Sep. 28, 2018

(86) PCT No.: PCT/EP2018/076446
§ 371 (c)(1),
(2) Date: Mar. 27, 2020

(87) PCT Pub. No.: WO2019/063786
PCT Pub. Date: Apr. 4, 2019

(65) Prior Publication Data
US 2020/0282130 A1 Sep. 10, 2020

Related U.S. Application Data

(60) Provisional application No. 62/565,348, filed on Sep. 29, 2017.

(51) Int. Cl.
*A61L 2/00* (2006.01)
*A61L 11/00* (2006.01)
(Continued)

(52) U.S. Cl.
CPC .............. *A61L 2/206* (2013.01); *A61M 5/001* (2013.01); *A61M 5/002* (2013.01); *A61M 5/315* (2013.01);
(Continued)

(58) Field of Classification Search
CPC .......... A61L 2/00; A61L 2/0094; A61L 2/206; A61L 2202/23
(Continued)

(56) References Cited

U.S. PATENT DOCUMENTS

2005/0075611 A1  4/2005  Hetzler et al.
2013/0296779 A1* 11/2013  Kuehne .............. A61M 5/3134
                                              604/93.01
2017/0106165 A1  4/2017  Holmes

FOREIGN PATENT DOCUMENTS

DE        24 58 004 A1    6/1976
JP      2006-271461 A    10/2006
(Continued)

OTHER PUBLICATIONS

International Search Report dated Dec. 17, 2018 in corresponding International Patent Application No. PCT/EP2018/076446.
(Continued)

*Primary Examiner* — Monzer R Chorbaji
(74) *Attorney, Agent, or Firm* — MEDLER FERRO WOODHOUSE & MILLS PLLC

(57) ABSTRACT

A method of preparing a prefilled syringe is disclosed that includes obtaining a syringe barrel and a needle adaptor cap assembled on the tip of the syringe barrel, wherein the needle adaptor cap has a rubber element tightly sealing the
(Continued)

orifice of the tip of the syringe barrel and the syringe barrel together with the needle adaptor cap assembled on the tip of the syringe barrel is sterilized by a first sterilizing. Filling a drug substance into an interior of the syringe barrel and sealing the interior of the syringe barrel. Packaging the syringe barrel with a rubber stopper sealing the interior thereof and the needle adaptor cap assembled on the tip of the syringe barrel. Providing a second external surface sterilizing of the packaged syringe barrel with the rubber stopper sealing the interior thereof and the needle adaptor cap assembled on the tip of the syringe barrel.

18 Claims, 1 Drawing Sheet

(51) Int. Cl.

| | |
|---|---|
| *A61L 2/20* | (2006.01) |
| *A61M 5/00* | (2006.01) |
| *A61M 5/31* | (2006.01) |
| *A61M 5/315* | (2006.01) |
| *A61M 5/32* | (2006.01) |
| *B65B 3/00* | (2006.01) |
| *B65B 7/28* | (2006.01) |
| *B65B 55/10* | (2006.01) |
| *B65B 55/02* | (2006.01) |

(52) U.S. Cl.
CPC ........ *A61M 5/3129* (2013.01); *A61M 5/3202* (2013.01); *B65B 3/003* (2013.01); *B65B 7/2821* (2013.01); *B65B 55/10* (2013.01); *A61L 2202/23* (2013.01); *A61L 2202/24* (2013.01); *A61M 5/31513* (2013.01); *A61M 2005/3104* (2013.01); *A61M 2005/3114* (2013.01); *A61M 2205/0238* (2013.01); *A61M 2207/00* (2013.01); *A61M 2207/10* (2013.01); *B65B 55/02* (2013.01)

(58) Field of Classification Search
USPC ...................................................... 422/1, 28
See application file for complete search history.

(56) References Cited

FOREIGN PATENT DOCUMENTS

| | | |
|---|---|---|
| JP | 2007-507308 A | 3/2007 |
| WO | 2005/032627 A1 | 4/2005 |
| WO | 2017/087871 A1 | 5/2017 |

OTHER PUBLICATIONS

Japanese Office Action issued in corresponding Japanese Application No. 2020-517591 dated Aug. 2, 2022.

* cited by examiner

PREFILLED SYRINGE AND METHOD OF PREPARING A PREFILLED SYRINGE

TECHNICAL FIELD

The present invention relates to a method of preparing a prefilled syringe and more particularly to a prefilled syringe obtained by such a method.

Such methods of preparing a prefilled syringe can be used for obtaining a prefilled sterile syringe such that it is suitable to be used for administering pharmaceutical or drug substances. They can comprise the steps of:

(i) assembling a needle adaptor cap on a tip of a syringe barrel having an open end and the tip with an orifice essentially opposite to the open end;

(ii) first sterilizing the syringe barrel together with the needle adaptor cap assembled on the tip of the syringe barrel, wherein the first sterilizing comprises a main step of exposing the syringe barrel together with the needle adaptor cap assembled on the tip of the syringe barrel to ethylene oxide at predefined conditions;

(iii) filling a drug substance through the open end of the syringe barrel into an interior of the syringe barrel;

(iv) sealing the interior of the syringe barrel by advancing a rubber stopper through the open end of the syringe barrel;

(v) packaging the syringe barrel together with the rubber stopper sealing the interior of the syringe barrel and the needle adaptor cap assembled on the tip of the syringe barrel; and (vi) second external surface sterilizing the external surface of the syringe barrel together with the rubber stopper sealing the interior of the syringe barrel and the needle adaptor cap assembled on the tip of the syringe barrel.

BACKGROUND ART

Many pharmaceutical products (below referred to as drugs or drug substances or drug solutions) are processed and/or administered in liquid form wherein injecting the drugs often is most efficient and preferred. Particularly for subcutaneous, intramuscular, intradermal or intravitreal injection the pharmaceutical substances are often provided in prefilled syringes (PFS) wherein such syringes may have the needles staked-in or are equipped with an adaptor for connecting a needle. In such syringes, the drug is provided in the interior of a barrel of the syringe in a solved or other liquid form ready for being administered. Like this, the user receives a (quasi) ready-to-inject syringe without the requirement to prepare and fill the drug into the syringe, e.g. by transferring the drug from a vial into a disposable syringe. The occurrence of particles and microbiological contaminations, injuries, and/or inappropriate or inconvenient handling during application can thereby be minimized.

Usually, prefilled syringes comprise a syringe barrel having an open end and a tip with an orifice essentially opposite to the open end, a rubber stopper, a plunger rod, an extended finger flange, and a needle adaptor cap with a rubber element. One common possibility for preparation of the PFS involves the following steps:

Assembling the needle adaptor cap on the tip of the syringe barrel wherein the rubber element of the needle adaptor cap tightly seals the orifice of the tip of the syringe barrel.

Sterilizing the assembly of syringe barrel and needle adaptor cap. Thereby, the assembly often is exposed to a sterilizing agent at well-defined conditions, such as sterilant concentration, temperature, duration, relative humidity and/or pressure, allowing a complete sterilization of the assembly even in between the rubber element of the needle adaptor cap and the tip of the syringe barrel. Frequently, ethylene oxide (EO) is used as sterilizing agent.

After this first sterilization, a sterile drug or drug solution is aseptically filled through the open end of the syringe barrel into an interior of the syringe barrel. Such aseptic filling typically is accomplished in cleanrooms in order to maintain sterility. Such cleanrooms are often classified, e.g., by the standards defined as "Sterile Drug Products Produced By Aseptic Processing" or "Manufacture of Sterile Medicinal Products" by Good Manufacturing Practice (GMP) for Active Pharmaceutical Ingredients (API) issued by the International Conference on Harmonisation Regulations. For many parenteral drug substances such as ophthalmic drugs for intravitreal injection, the cleanrooms have to conform to the provisions for class A of the GMP standards.

After aseptically filling the drug, the interior of the syringe barrel is sealed by advancing the sterile rubber stopper through the open end of the syringe barrel. This step typically is, again, accomplished aseptically in the cleanrooms.

The sealed assembly is then typically moved out of the cleanroom and provided with the plunger rod and eventually with further elements such as, e.g., an extended finger flange and the like.

For ophthalmic device combination product, after the PFS being composed and eventually packaged, external surface of the syringe assembly must be sterilized. Thereby, in order to prevent the drug inside the syringe barrel to be affected, it can be important to prevent that the sterilizing agent enters the interior of the syringe barrel. In particular, ingress of the sterilizing agent should be below the limit provided by health authorities or the International Organization for Standardization (ISO), or must not compromise the drug quality until end of shelf life. For example, the European Agency for the Evaluation of Medicinal Products (EMEA) specifies in EMEA/CVMP/271/01 guidance a limit of 1 µg/mL EO and 50 µg/mL ethylene chloride (EG). Or, ISO10993-7 specifies a limit of 0.5 µg EO/IOL/24 hr and 1.25 µg EO/IOL, which interprets 0.5 µg EO/eye/24 hr and 1.25 µg EO/eye.

Thus, typically, during preparation of PFS for ophthalmic use two subsequent sterilizations are performed, a first one before filling the drug and a second final external surface sterilization once the PFS is completely assembled. Thereby, the aim or extent of sterilization is different in these two sterilizations. In the first complete sterilization, the sterilizing agent is aimed to get through the rubber element and/or through its interface with the tip of the syringe barrel. Therefore, for the first sterilization the rubber element is aimed to have a certain gas permeability for the sterilizing agent. In the second external surface sterilization, however, it is crucial that the rubber element has a comparably low gas permeability for any gas or other substance such that a high drug quality can be maintained. Therefore, for the second external surface sterilization the rubber element is aimed to have a minimal gas permeability.

In the light of this challenge or of these counter requirements involved in the first and second external surface sterilizations, there is a need for a method of preparing a prefilled syringe allowing complete and efficient first and second external surface sterilization and for a sterile prefilled syringe having a tightly sealed interior of its syringe barrel.

DISCLOSURE OF THE INVENTION

According to the invention, this need is settled by a method and a prefilled syringe as described herein.

In particular, in one embodiment, the invention is a method of preparing a prefilled syringe (PFS), comprising: (i) obtaining a syringe barrel having an open end and a tip with an orifice essentially opposite to the open end, and a needle adaptor cap assembled on the tip of the syringe barrel, wherein the needle adaptor cap has a rubber element tightly sealing the orifice of the tip of the syringe barrel, and the syringe barrel together with the needle adaptor cap assembled on the tip of the syringe barrel is sterilized by a first sterilizing comprising a main step of exposing the syringe barrel together with the needle adaptor cap assembled on the tip of the syringe barrel to ethylene oxide ($C_2H_4O$ or EO) for about 5 hours to about 60 hours at a relative humidity of about 40% to about 100% and at a temperature of about 30° C. to about 60° C.; (ii) filling a drug substance through the open end of the syringe barrel or the orifice of the syringe barrel into an interior of the syringe barrel; (iii) sealing the interior of the syringe barrel by advancing a rubber stopper through the open end of the syringe barrel; (iv) packaging the syringe barrel together with the rubber stopper sealing the interior of the syringe barrel and the needle adaptor cap assembled on the tip of the syringe barrel; and (v) second external surface sterilizing the packaged syringe barrel together with the rubber stopper sealing the interior of the syringe barrel and the needle adaptor cap assembled on the tip of the syringe barrel.

For allowing an efficient second external surface sterilizing, the packaging advantageously is EO gas permeable. Such packaging allows for maintaining sterility, protecting and easy handling of the syringe.

The term "drug" as used herein relates to a therapeutically active agent, also commonly called active pharmaceutical ingredient (API), as well as to a combination of plural such therapeutically active substances. The term also encompasses diagnostic or imaging agents, like for example contrast agents (e.g. MRI contrast agents), tracers (e.g. PET tracers) and hormones, that need to be administered in liquid form to the patient.

The term "drug substance" as used herein relates to a drug as defined above formulated or reconstituted in a form that is suitable for administration to the patient. For example, besides the drug, a drug substance may additionally comprise an excipient and/or other auxiliary ingredients. A particularly preferred drug substance in the context of the invention is a drug solution, in particular a solution for oral administration, injection or infusion.

The term "drug product" as used herein relates to a finished end product comprising a drug substance or a plurality of drug substances. In particular, a drug product may be a ready to use product having the drug substance in an appropriate dosage and/or in an appropriate form for administration. For example, a drug product may include an administration device such as a prefilled syringe or the like.

In order to allow the drug substance to be filled through the orifice while being sealed by the rubber element, the needle adaptor cap and particularly its rubber element can be appropriately embodied. For example, the rubber element can be septum-like formed and the cap can be provided with an access passage for allowing a supplying needle to fill the drug substance through the orifice via the access passage and the rubber element.

The term "sterile" as used herein relates to a maximum contamination rate allowing the syringe or another element to be used in an intended application. For example, it can relate to a state of the PFS conforming with the requirements and guidance according to the Standard ST67 of the American National Standards Institute (ANSI) and the Association for the Advancement of Medical Instrumentation (AAMI), i.e. to ANSI/AAMI ST67. More particularly, sterile can mean to conform with level 6 specified in ANSI/AAMI ST67. Analogously, the term "sterilize" relates to bringing a structure or element such as the PFS in a sterile state.

More particularly, the term "sterile" can be directed to achieving a situation free of any viable organisms. In particular, sterilization can relate to a validated process used to render a product essentially free of viable organisms. In such a sterilization process, the nature of microbiological death of reduction can be described by an exponential function. Therefore, the number of microorganisms which survive a sterilization process can be expressed in terms of probability. While the probability may be reduced to a very low number, it can not be reduced to zero.

The filling of the drug substance and the sealing of the interior of the syringe barrel are typically performed aseptically or in an aseptic environment. When the drug is filled through the orifice, the rubber stopper can be placed in the syringe barrel already. In particular, the rubber stopper can be advanced into the syringe barrel as far as possible and, when filling the drug through the orifice, the rubber stopper can be pushed back as far as required. Like this, the risk of bubbles in the drug can be reduced or eliminated.

The rubber element of the needle adaptor cap and the rubber stopper are made of a rubber material having an oxygen transmission rate at 1 atmosphere (atm), corresponding to 101325 Pascal (Pa), of not more than 120 cubic centimeter per square meter and day ($cm^3/(m^2*d)$), of between 115 $cm^3/(m^2*d)$ and 116 $cm^3/(m^2*d)$, of not more than 110 $cm^3/(m^2*d)$, of not more than 100 $cm^3/(m^2*d)$, of not more than 90 $cm^3/(m^2*d)$, of not more than 80 $cm^3/(m^2*d)$, of not more than 70 $cm^3/(m^2*d)$, of not more than 65 $cm^3/(m^2*d)$, of between 63 $cm^3/(m^2*d)$ and 64 $cm^3/(m^2*d)$, or of about 63.6 $cm^3/(m^2*d)$.

The second external surface sterilizing comprises a main step of exposing the packaged syringe barrel together with the rubber stopper sealing the interior of the syringe barrel and the needle adaptor cap assembled on the tip of the syringe barrel to EO for about 3 hours to about 30 hours at a relative humidity of about 40% to about 100% and at a temperature of about 25° C. to about 45° C.

At least one of the duration, the relative humidity and the temperature of the second external surface sterilizing is essentially lower than the respective duration, relative humidity or temperature of the first sterilization. In this connection, the term "essentially lower" relates to a difference sufficient for allowing the EO to permeate the sealing of the tip by the rubber element in the first sterilizing and for preventing the EO to permeate the sealing of the tip by the rubber element and sealing of the interior of the syringe barrel by the rubber stopper in the second external surface sterilizing. In relative numbers, such essentially lower can relate to a difference of at least about 5%, at least about 10%, at least about 20%, at least about 30% or at least about 40%. In absolute numbers, it can relate to a difference of at least about 2 h, at least about 5 h, at least about 10 h or at least about 15 h for the duration, to at least about 5%, at least about 10%, at least about 15% or at least about 20% for the relative humidity and/or to at least about 5° C., to at least about 10° C., to at least about 15° C. or to at least about 20° C. for the temperature. Advantageously, not only one but plural or preferably all of the above parameters are lower in the second external surface sterilizing than in the first sterilizing. If plural parameters of the second external surface sterilizing are lower than the respective parameters of the first sterilizing at the same time, their differences might also be lower in order to achieve an essential difference in the sense of the invention.

The prefilled syringe can particularly be an ophthalmic prefilled syringe for intravitreal injection of the drug substance. In such administrations, the requirements as to sterility and contamination can be particularly high. Therefore, in such treatments, tight sealing of the syringe barrel often is highly important and the demands to the syringe in terms of sterility are also comparably high.

In accordance with the invention, using a rubber material for the rubber element of the needle adaptor cap and the rubber stopper, which has a gas permeability in the defined ranges or values, allows for providing an advantageous tightness of the syringe barrel such that the drug substance inside of it can be protected from contaminations or other affecting impacts. Additionally, providing EO under the conditions defined above for the first sterilization allows for completely sterilizing the syringe barrel with the adaptor cap even at locations between the rubber element and the orifice of the syringe barrel even though the rubber element comparably tightly seals the orifice. At the same time providing EO under the conditions defined above for the second external surface sterilization allows for preventing EO to enter the interior of the syringe barrel such that drug substance is not affected by the second external surface sterilizing. The difference in applicable parameter ranges for first and second external surface sterilization is determined by the rubber formulations and rubber designs in the cap and in the barrel.

Thus, the method according to the invention allows for preparing a prefilled syringe including complete and efficient first and second external surface sterilization from which results a prefilled syringe having a tightly sealed and sterile interior of its syringe barrel.

Preferably, obtaining the syringe barrel and the needle adaptor cap assembled on the tip of the syringe barrel comprises: (a) assembling the needle adaptor cap on the tip of the syringe barrel; and (b) first sterilizing the syringe barrel together with the needle adaptor cap assembled on the tip of the syringe barrel, wherein the first sterilizing comprises the main step of exposing the syringe barrel together with the needle adaptor cap assembled on the tip of the syringe barrel to EO for about 5 hours to about 60 hours at a relative humidity of about 40% to about 100% and at a temperature of about 30° C. to about 60° C.

The initial preparation step (i) above can be performed by the manufacturer of the syringe, which often is different from the manufacturer of the drug substance in the end marketing the PFS. In such situations, the sterilized assembly can be packaged and furnished to the drug manufacturer. Alternatively, this step (i) can also be performed by the drug manufacturer himself.

Thus, in another embodiment, the invention is a method of preparing a prefilled syringe, comprising: (i) assembling a needle adaptor cap on a tip of the syringe barrel having an open end and the tip with an orifice essentially opposite to the open end; (ii) first sterilizing the syringe barrel together with the needle adaptor cap assembled on the tip of the syringe barrel, wherein the first sterilizing comprises the main step of exposing the syringe barrel together with the needle adaptor cap assembled on the tip of the syringe barrel to EO for about 5 hours to about 60 hours at a relative humidity of about 40% to about 100% and at a temperature of about 30° C. to about 60° C.; (iii) filling a drug substance through the open end of the syringe barrel or the orifice of the syringe barrel into an interior of the syringe barrel; (iv) sealing the interior of the syringe barrel by advancing a rubber stopper through the open end of the syringe barrel; (v) packaging the syringe barrel together with the rubber stopper sealing the interior of the syringe barrel and the needle adaptor cap assembled on the tip of the syringe barrel; and (vi) second external surface sterilizing the packaged syringe barrel together with the rubber stopper sealing the interior of the syringe barrel and the needle adaptor cap assembled on the tip of the syringe barrel In the other embodiment, the rubber element of the needle adaptor cap and the rubber stopper are also made of a rubber material having an oxygen transmission rate at 1 atm of not more than 120 $cm^3/(m^2*d)$, of between 115 $cm^3/(m^2*d)$ and 116 $cm^3/(m^2*d)$, of not more than 110 $cm^3/(m^2*d)$, of not more than 100 $cm^3/(m^2*d)$, of not more than 90 $cm^3/(m^2*d)$, of not more than 80 $cm^3/(m^2*d)$, of not more than 70 $cm^3/(m^2*d)$, of not more than 65 $cm^3/(m^2*d)$, of between 63 $cm^3/(m^2*d)$ and 64 $cm^3/(m^2*d)$, or of about 63.6 $cm^3/(m^2*d)$.

Further, in the other embodiment, the second external surface sterilizing also comprises a main step of exposing the syringe barrel together with the rubber stopper sealing the interior of the syringe barrel and the needle adaptor cap assembled on the tip of the syringe barrel to EO for about 3 h to about 30 h at a relative humidity of about 40% to about 100% and at a temperature of about 25° C. to about 45° C.

Still further, in the other embodiment, at least one of the duration, the relative humidity and the temperature of the second external surface sterilizing is essentially lower than the respective duration, relative humidity or temperature of the first sterilization.

In the following, preferred features of both embodiments of the method for preparing a prefilled syringe illustrated above are described defining preferred embodiments of the invention.

Preferably, the main step of the first sterilizing is performed in a sterilization chamber. In this connection, the term "sterilization chamber" can relate to chambers allowing for providing conditions appropriate for sterilization. In particular, such chambers may be capable of achieving a pressure different from ambient air, temperatures different from ambient temperatures and a specific relative humidity of any selected agents. Advantageously, such chambers allow for adjusting and changing the conditions of their interiors. By using a sterilization chamber for performing the first sterilization, the conditions can be efficiently and precisely tuned and adjusted to be appropriate.

Preferably, the main step of the first sterilizing further comprises exposing the syringe barrel together with the needle adaptor cap assembled on the tip of the syringe barrel to a pressure of about 450 millibars (mbar) to about 1'000 mbar. Additionally or alternatively, in the main step of the first sterilizing, the ethylene oxide preferably is provided in a concentration of about 400 milligrams per liter (mg/l) to about 800 mg/l. Such a pressure and/or EO concentration allows for further improving the first sterilizing such that its efficiency can be increased without harming any components of the syringe assembly such as, e.g., the rubber element of the needle adaptor cap.

Preferably, the main step of the first sterilizing comprises flushing the syringe barrel together with the needle adaptor cap assembled on the tip of the syringe barrel with air, nitrogen or a combination thereof at a pressure of about 100 mbar or about 200 mbar to about 800 mbar or about 900 mbar after exposing the syringe barrel together with the needle adaptor cap to ethylene oxide. Such flushing after EO exposition allows for bringing the syringe barrel and needle adaptor cap assembly in a condition to be removed from the sterilization or similar chamber. In particular, the flushing allows to clean the sterilization chamber and/or the assembly such that the sterilization chamber can be opened without exposing the person opening the chamber to any risk.

The main step of the first sterilizing preferably further comprises exposing the syringe barrel together with the needle adaptor cap assembled on the tip of the syringe barrel to a pressure of about 50 mbar to about 200 mbar. Advantageously, such pressure exposition is performed prior to exposing the assembly to EO. This pre-pressurization can be helpful for preparing the syringe before the actual sterilization.

In one preferred embodiment, the first sterilizing comprises a pre-conditioning step of exposing the syringe barrel together with the needle adaptor cap assembled on the tip of the syringe barrel to ethylene oxide for about 12 hours (h) to about 96 h at a relative humidity of about 40% to about 100% and at a temperature of about 30° C. to about 60° C., wherein the pre-conditioning step of the first sterilizing is executed prior the main step of the first sterilizing. This pre-conditioning step of the first sterilizing preferably is performed outside the sterilization chamber. Such pre-conditioning allows for efficiently putting the syringe barrel and needle adaptor cap assembly in place to be efficiently sterilized in the main step of the first sterilizing. In particular, it allows for achieving a comparably well wettability of the rubber element of the needle adaptor cap. By performing this comparably time-consuming step outside the sterilization chamber, the utilization of the chamber can be optimized such that the overall process efficiency can be increased.

In another preferred embodiment, the first sterilizing comprises a pre-conditioning step of exposing the syringe barrel together with the needle adaptor cap assembled on the tip of the syringe barrel to ethylene oxide for about 10 minutes (min) to about 2 h at a relative humidity of about 40% to about 100% and at a temperature of about 30° C. to about 60° C., wherein the pre-conditioning step of the first sterilizing is executed prior the main step of the first sterilizing. This pre-conditioning step of the first sterilizing preferably is performed inside the sterilization chamber. Such alternative pre-conditioning also allows for efficiently putting the syringe barrel and needle adaptor cap assembly in place to be efficiently sterilized in the main step of the first sterilization. In particular, it allows achieving a comparably well wettability of the rubber element of the needle adaptor cap. However, by performing this step inside the sterilization chamber, the time required for pre-conditioning can essentially be lowered. This may also allow for increasing the overall process efficiency.

Preferably, the first sterilizing further comprises an aeration step of exposing the syringe barrel together with the needle adaptor cap assembled on the tip of the syringe barrel to an air flow for about 12 h to about 96 h at a temperature of about 30° C. to about 60° C., wherein the aeration step of the first sterilizing is executed after the main step of the first sterilizing. This step allows removing residuals on the syringe barrel and needling adaptor cap assembly. It can be performed inside or outside the sterilization chamber.

Preferably, the main step of the second external surface sterilizing is performed in a sterilization chamber. The sterilization chamber used in the main step of the second external surface sterilizing can be different from, the same as, or of the same type as the sterilization chamber used in the main step of the first sterilizing. Using the sterilization chamber for the second external surface sterilization allows for efficiently and precisely adjusting and providing the conditions required for the second external surface sterilizing being different from the conditions of the first sterilizing.

Preferably, the main step of the second external surface sterilizing comprises exposing the syringe barrel together with the rubber stopper sealing the interior of the syringe barrel and the needle adaptor cap assembled on the tip of the syringe barrel to a pressure of about 450 mbar to about 1000 mbar. Such increased pressure allows for achieving an appropriate sterilization yield wherein it can be prevented that the EO completely permeates the sealing of the tip of the syringe barrel by the rubber element of the needle adaptor cap. Further, in the main step of the second external surface sterilizing the EO preferably is provided in a concentration of about 400 mg/l to about 800 mg/l. Such concentration of EO allows for efficiently sterilizing the external surface of the PFS.

At least one of the pressure and the concentration of the second external surface sterilizing can be essentially lower than the respective pressure or concentration of the first sterilization. Similar as above, the term "essentially lower" relates to a difference sufficient for allowing the EO to permeate the sealing of the tip by the rubber element in the first sterilizing and for preventing the EO to permeate the sealing of the tip by the rubber element and sealing of the interior of the syringe barrel by the rubber stopper in the second external surface sterilizing. In relative numbers, such essentially lower can relate to a difference of at least about 5%, at least about 10%, at least about 20%, at least about 30% or at least about 40%. In absolute numbers, it can relate to a difference of at least about 50 mbar, at least about 100 mbar, at least about 150 mbar or at least about 200 mbar for the pressure and/or to at least about 50 mg/l, at least about 100 mg/l, at least about 150 mg/l or at least about 200 mg/l for the concentration.

Preferably, the main step of the second external surface sterilizing further comprises flushing the syringe barrel together with the rubber stopper sealing the interior of the syringe barrel and the needle adaptor cap assembled on the tip of the syringe barrel with air, nitrogen or a combination thereof at a pressure of about 100 mbar or about 200 mbar to about 800 mbar or about 900 mbar after exposing the syringe barrel together with the rubber stopper sealing the interior of the syringe barrel and the needle adaptor cap assembled on the tip of the syringe barrel to ethylene oxide. As described for the first sterilization above, such flushing after EO exposition allows for bringing the PFS in a condition to be removed from the sterilization or similar chamber. Like this, the PFS can efficiently be further processed or used such as stored or delivered.

Also, the main step of the second external surface sterilizing preferably comprises exposing the syringe barrel together with the rubber stopper sealing the interior of the syringe barrel and the needle adaptor cap assembled on the tip of the syringe barrel to a pressure of about 50 mbar to about 200 mbar. Advantageously, such pressure exposition is performed prior to exposing the PFS to EO. This pre-pressurization can be helpful for preparing the syringe before the actual sterilization.

In one preferred embodiment, the second external surface sterilizing comprises a pre-conditioning step of exposing the syringe barrel together with the rubber stopper sealing the interior of the syringe barrel and the needle adaptor cap assembled on the tip of the syringe barrel to ethylene oxide for about 12 h to about 96 h at a relative humidity of about 40% to about 100% and at a temperature of about 25° C. to about 45° C., wherein the pre-conditioning step of the second external surface sterilizing is executed prior the main step of the second external surface sterilizing. This pre-conditioning step of the second external surface sterilizing preferably is performed outside the sterilization chamber. Such pre-conditioning allows for efficiently putting the PFS in place to be efficiently sterilized in the main step of the second external surface sterilization. In particular, it allows achieving a comparably well wettability of the rubber element of the needle adaptor cap as well as of the rubber stopper. By performing this comparably time-consuming step outside the sterilization chamber, the utilization of the chamber can be optimized such that the overall process efficiency can be increased.

In another preferred embodiment, the second external surface sterilizing comprises a pre-conditioning step of exposing the syringe barrel together with the rubber stopper sealing the interior of the syringe barrel and the needle adaptor cap assembled on the tip of the syringe barrel to ethylene oxide for about 10 min to about 2 h at a relative humidity of about 40% to about 100% and at a temperature of about 25° C. to about 45° C., wherein the pre-conditioning step of the second external surface sterilizing is executed prior the main step of the second external surface sterilizing. This pre-conditioning step of the second external surface sterilizing preferably is performed inside the sterilization chamber. Such alternative pre-conditioning also allows for efficiently putting the PFS in place to be efficiently sterilized in the main step of the second external surface sterilization. In particular, it allows achieving a comparably well wettability of the rubber element of the needle adaptor cap as well as of the rubber stopper. However, by performing this step inside the sterilization chamber, the time required for pre-conditioning can essentially be lowered. This may also allow for increasing the overall process efficiency.

Preferably, the second external surface sterilizing comprises an aeration step of exposing the syringe barrel together with the rubber stopper sealing the interior of the syringe barrel and the needle adaptor cap assembled on the tip of the syringe barrel to an air flow for about 12 h to about 96 h at a temperature of about 25° C. to about 45° C., wherein the aeration step of the second external surface sterilizing is executed after the main step of the second external surface sterilization. Such aeration allows for removing residuals on the PFS. It can be performed inside or outside the sterilization chamber.

Preferably, the filling of the drug substance into the interior of the syringe barrel and the sealing of the open end of the syringe barrel are performed in a cleanroom. In this connection, the term "cleanroom" relates to an environment, typically used in manufacturing, with a comparably low level of environmental pollutants such as dust, airborne microbes, aerosol particles, and chemical vapors. Thereby, a cleanroom can have a controlled level of contamination that is specified by the number of particles per cubic meter at a specified particle size. Typically, such cleanrooms are classified, e.g., by the standards defined as "Sterile Drug Products Produced By Aseptic Processing" or "Manufacture of Sterile Medicinal Products" by Good Manufacturing Practice (GMP) for Active Pharmaceutical Ingredients (API) issued by the International Conference on Harmonisation Regulations. For many drug substances such as ophthalmic drugs to be injected directly into the eye, the cleanrooms have to conform to the provisions for class A of the GMP standards. Drug sterility is maintained by aseptically filling the sterile drug substance into the syringe in a class A or clean area classification 100 cleanroom.

Thereby, the second external surface sterilizing preferably is performed outside the cleanroom. Like this, the time the cleanroom is required can be lowered. Usually, operating a cleanroom involves a comparably high effort and is comparably costly, reducing the time in the process in which the cleanroom is required allows for increasing efficiency.

Preferably, after the sealing of the open end of the syringe barrel, an auxiliary component is mounted to the syringe barrel. In this connection, the term "auxiliary component" relates to any part provided to complete the PFS. In particular, such auxiliary component can be any combination of a plunger rod inserted into the open end of the syringe barrel, an extended finger flange attached to the syringe barrel or a dosing device for adjusting a dose to be injected. This step in the process allows the assembled or complete and packaged PFS to undergo the second external surface sterilization. Like this, the PFS can be provided ready to use also in applications where overall sterility is crucial such as in ophthalmic applications.

Another aspect of the invention relates to a prefilled syringe (PFS) comprising: (i) a syringe barrel having an open end and a tip with an orifice essentially opposite to the open end; (ii) a needle adaptor cap assembled on the tip of the syringe barrel, wherein the needle adaptor cap has a rubber element tightly sealing the orifice of the tip of the syringe barrel and the syringe barrel together with the needle adaptor cap assembled on the tip of the syringe barrel; (iii) a rubber stopper sealing an interior of the syringe barrel; and (iv) a drug substance arranged in the interior of the syringe barrel. The rubber element of the needle adaptor cap and the rubber stopper are made of a rubber material having an oxygen transmission rate at 1 atm of not more than 120 $cm^3/(m^2{*}d)$, of between 115 $cm^3/(m^2{*}d)$ and 116 $cm^3/(m^2{*}d)$, of not more than 110 $cm^3/(m^2{*}d)$, of not more than 100 $cm^3/(m^2{*}d)$, of not more than 90 $cm^3/(m^2{*}d)$, of not more than 80 $cm^3/(m^2{*}d)$, of not more than 70 $cm^3/(m^2{*}d)$, of not more than 65 $cm^3/(m^2{*}d)$, of between 63 $cm^3/(m^2{*}d)$ and 64 $cm^3/(m^2{*}d)$, or of about 63.6 $cm^3/(m^2{*}d)$. The PFS is prepared by a method as it is described above. Like this, a PFS can be provided which is advantageous in terms of tightness of the interior of the syringe barrel. In addition, such a syringe can be provided with sterile inside and outside surfaces. This allows the PFS to be used for sensitive administration of drugs at sensitive locations. In particular, it allows an ophthalmic drug to be injected directly into an eye. Thus, the PFS can be an ophthalmic PFS and can have a syringe barrel volume of about 1 ml or less, or about 0.5 ml or less.

BRIEF DESCRIPTION OF THE DRAWINGS

The method and prefilled syringe according to the invention are described in more detail herein below by way of exemplary embodiments and with reference to the attached drawings, in which.

DESCRIPTION OF EMBODIMENTS

In the following description, certain terms are used for reasons of convenience and are not intended to limit the invention. The terms "right", "left", "up", "down", "under"

and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
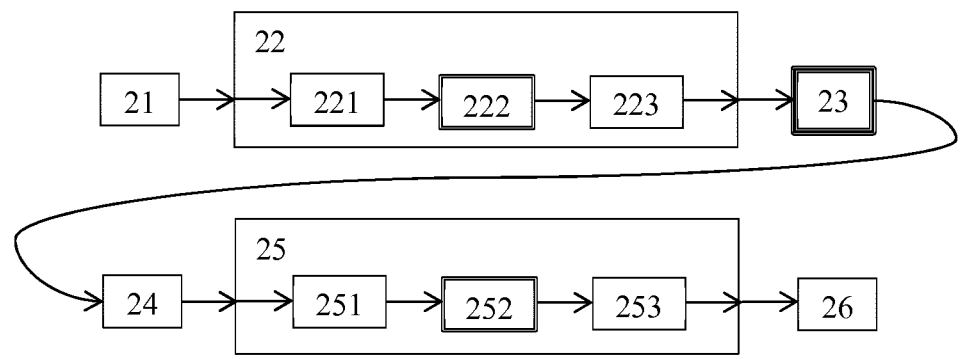
FIG. 1 shows a flow chart of an embodiment of a method according to the invention.

FIG. 1 shows an embodiment of a method for preparing a PFS 2 according to the invention. In a first step 21 syringe components are obtained and washed as well as siliconized. The components comprise a syringe barrel having an open end and a tip with an orifice essentially opposite to the open end. They further comprise a needle adaptor cap with a rubber element. The rubber element is made of a rubber material having an oxygen transmission rate at 1 atm of 63.6 cm$^3$/(m$^2$*d). In the first step 21, the needle adaptor cap is assembled on the tip of the syringe barrel such that the orifice of the tip is tightly sealed by the rubber element.

In a second step 22 the syringe barrel together with the needle adaptor cap assembled on the tip of the syringe barrel, in the following referred to as assembly, is first sterilized. Thereby, the first sterilizing 22 comprises a pre-conditioning step 221, a main step 222 and an aeration step 223.

In the pre-conditioning step 221 of the first sterilizing 22, the assembly is exposed to EO for about 52 hours at a relative humidity of about 60% and at a temperature of about 50° C. The pre-conditioning step 221 of the first sterilizing 22 is performed in a separate environment.

Then the assembly is transferred into a sterilization chamber for the main step 222 of the first sterilizing 22. There, the assembly is initially exposed to a pressure of about 150 mbar for preparing the assembly and particularly the rubber element of the needle adaptor cap. Then, the assembly is exposed to vaporized EO in a concentration of about 700 mg/l for about 25 hours at a relative humidity of about 90%, at a temperature of about 55° C. and at a pressure of about 900 mbar. Before removing the assembly from the sterilization chamber, it is flushed with a nitrogen-air-combination wherein the pressure is continuously raised and lowered between about 150 mbar and about 850 mbar. Like this, the EO can widely be removed from the assembly.

After flushing the assembly, it is taken out of the sterilization chamber and treated in the aeration step 223 of the first sterilizing 22. Thereby, the assembly is exposed to air at a temperature of about 45° C. for about 55 h. In the aeration step 223 essentially all residuals of the first sterilization are removed. With the aeration step 223, the first sterilizing ends.

The assembly is then transferred into a class A cleanroom where in a sterile or aseptic environment a filling step 23 is executed. In the filling step 23, a precise amount of an ophthalmic drug solution is filled into the interior of the syringe barrel via its open end. Once the correct amount of the drug is in the interior of the syringe barrel, it is tightly closed by providing a rubber stopper through the open end of the syringe barrel into its interior. The rubber stopper is made of the same rubber material as the rubber element of the needle adaptor cap which has an oxygen transmission rate at 1 atm of 63.6 cm$^3$/(m$^2$*d).

The sealed assembly with the drug solution is then removed from the cleanroom. There, in a mounting step 24 a plunger rod is pushed through the open end of the syringe barrel and is coupled to the rubber stopper inside the interior of the syringe barrel. Also, the syringe barrel is provided with an extended finger flange for better handling of the syringe and the prefilled syringe (PFS) is finished. The PFS is then blistered for packaging. The blister packaging material has a comparably high permeability for EO.

Afterwards, the blister package containing the PFS is second external sterilized 25. Thereby, the second external surface sterilizing 25 comprises a pre-conditioning step 251, a main step 252 and an aeration step 253.

In the pre-conditioning step 251, the PFS is exposed to EO for about 55 h at a relative humidity of about 60% and at a temperature of about 30° C. The pre-conditioning step 251 of the second external surface sterilizing 25 is performed in a separate environment.

After being pre-conditioned, the PFS is transferred to a sterilization chamber in which the main step 252 of the second external surface sterilizing 25 is executed. There, the packaged PFS is initially exposed to a pressure of about 150 mbar for particularly preparing the rubber element of the needle adaptor cap and the rubber stopper. Then, the packaged PFS is exposed to vaporized EO in a concentration of about 500 mg/l for about 10 hours at a relative humidity of about 50%, at a temperature of about 30° C. and at a pressure of about 550 mbar. In order to allow the EO to reach the PFS, the blister packaging is gas permeable to EO. Before removing the PFS from the sterilization chamber, it is flushed with a nitrogen-air-combination wherein the pressure is continuously raised and lowered between about 150 mbar and about 550 mbar. Like this, the EO can widely be removed from the PFS.

After flushing, the PFS is taken out of the sterilization chamber and treated in the aeration step 253 of the second external surface sterilizing 25. Thereby, the PFS is exposed to air at a temperature of about 45° C. for about 55 h. In the aeration step 253 essentially all residuals of the second external surface sterilizing are removed from the PFS. With the aeration step 253, the second external surface sterilizing ends.

After aeration, in a last step 26 the PFS is then stored, sold, delivered and in the end used for administrating the drug solution.

Figure 2:
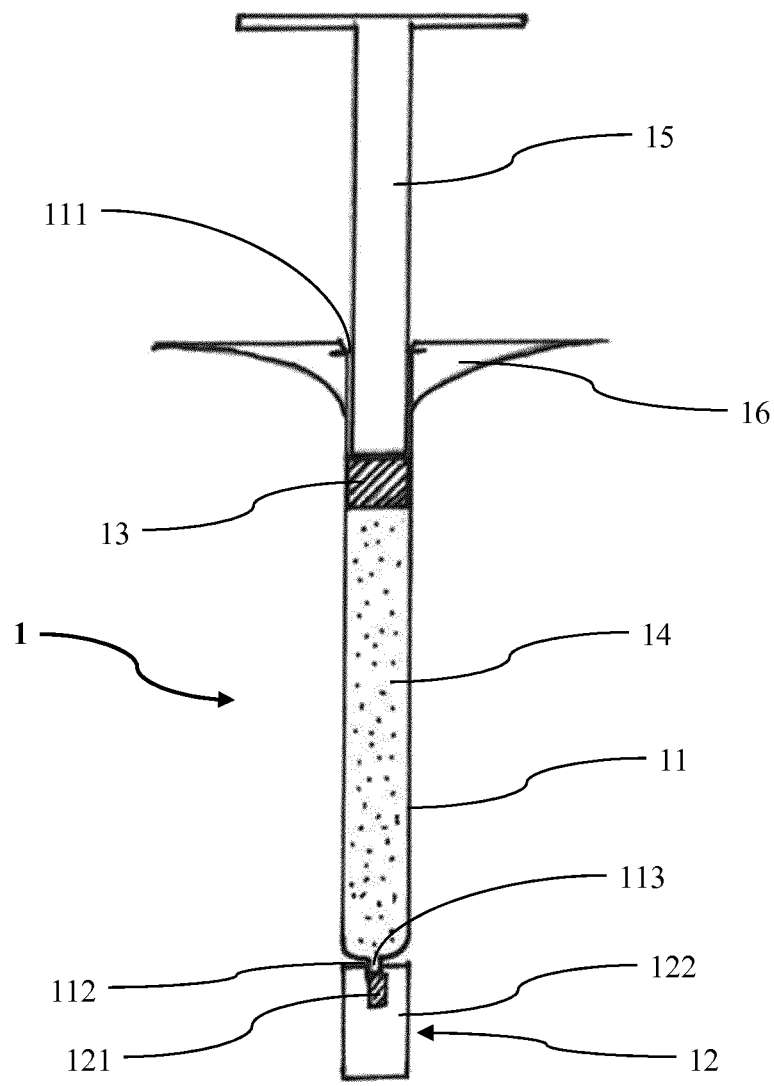
FIG. 2 shows a schematic side view of an embodiment of a prefilled syringe according to the invention.

FIG. 2 shows an embodiment of a prefilled syringe (PFS) 1 according to the invention obtained by the method described above in connection with FIG. 1. The PFS 1 comprises a syringe barrel 11, a needle adaptor cap 12, a rubber stopper 13, a liquid ophthalmic drug solution 14, a plunger rod 15 and an extended finger flange 16. The syringe barrel 11 has an open end 111 and a tip 112 with an orifice 113 opposite to the open end 111. The needle adaptor cap 12 has a rigid adaptor shell 122 and an elastic rubber element 121 inside the adaptor shell 122. It is assembled on the tip 112 of the syringe barrel 11 such that the rubber element 121 tightly seals the orifice 113 of the tip 112. In particular, the rubber element 121 is pressed onto the outer or lower end of the orifice 113 by mounting the adaptor shell 122 to the tip 112 such that the orifice 113 is closed and sealed. The adaptor shell 122 protects the rubber element 121 and provides an adaptor structure such as a Luer-Lock structure for mounting a needle to the PFS 1 before administration (not visible in FIG. 2). Even though in FIG. 2 the adaptor shell 122 is schematically represented as a single piece, it is understood that typically it is a two or multi part unit.

The drug solution 14 is arranged in an interior of the syringe barrel 11 which interior is sealed by the rubber stopper 13 advanced through the open end 111 of the syringe barrel 11 into an upper portion of the interior of the syringe barrel 11. Extending through the open end 111 of the syringe barrel lithe plunger rod 15 extends into the interior of the syringe barrel 11 such that the proximal end of the plunger rod 15 is adjacent to the rubber stopper 13. At the open end 111 the extended finger flange 16 is mounted to the syringe barrel 11 for a convenient handling of the PFS 1.

The method according to the invention allows that the rubber stopper 13 and the rubber element 121 of the needle adaptor cap 12 are made of a rubber material having advantageous properties. In particular, the rubber material of the rubber stopper 13 and the rubber element 121 has an oxygen transmission rate at 1 atm of 63.6 cm$^3$/(m$^2$*d). For example, such rubber material can be the rubber formulation 4023/50 comprising Bromobutyl and Silicate which is marketed by West Pharmaceutical Services, Inc.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be mechanically directly coupled, or they may be indirectly coupled via one or more intermediate components. Any reference signs in the claims should not be construed as limiting the scope.

The invention claimed is:

1. A method of preparing a prefilled syringe, comprising:
obtaining a syringe barrel having an open end and a tip with an orifice essentially opposite to the open end, and a needle adaptor cap assembled on the tip of the syringe barrel, wherein the needle adaptor cap has a rubber element tightly sealing the orifice of the tip of the syringe barrel, and the syringe barrel together with the needle adaptor cap assembled on the tip of the syringe barrel is sterilized by a first sterilizing comprising a main step of exposing the syringe barrel together with the needle adaptor cap assembled on the tip of the syringe barrel to ethylene oxide for about 5 hours to about 60 hours at a relative humidity of about 40% to about 100% and at a temperature of about 30° C. to about 60° C.;
filling a drug substance through the open end of the syringe barrel or through the orifice of the syringe barrel into an interior of the syringe barrel;
sealing the interior of the syringe barrel by advancing a rubber stopper through the open end of the syringe barrel;
packaging the syringe barrel together with the rubber stopper sealing the interior of the syringe barrel and the needle adaptor cap assembled on the tip of the syringe barrel, and
second external surface sterilizing the packaged syringe barrel together with the rubber stopper sealing the interior of the syringe barrel and the needle adaptor cap assembled on the tip of the syringe barrel,
wherein
the rubber element of the needle adaptor cap and the rubber stopper are made of a rubber material having an oxygen transmission rate at 1 atmosphere of not more than 120 cubic centimeter per square meter and day, of between 115 cubic centimeter per square meter and day and 116 cubic centimeter per square meter and day, of not more than 110 cubic centimeter per square meter and day, of not more than 100 cubic centimeter per square meter and day, of not more than 90 cubic centimeter per square meter and day, of not more than 80 cubic centimeter per square meter and day, of not more than 70 cubic centimeter per square meter and day, of not more than 65 cubic centimeter per square meter and day, of between 63 cubic centimeter per square meter and day and 64 cubic centimeter per square meter and day, or of about 63.6 cubic centimeter per square meter and day, the second external surface sterilizing comprises a main step of exposing the packaged syringe barrel together with the rubber stopper sealing the interior of the syringe barrel and the needle adaptor cap assembled on the tip of the syringe barrel to ethylene oxide for about 3 hours to about 30 hours at a relative humidity of about 40% to about 100% and at a temperature of about 25° C. to about 45° C., and at least one of the duration, the relative humidity and the temperature of the second external surface sterilizing is essentially lower than the respective duration, relative humidity or temperature of the first sterilizing.

2. The method of claim 1, wherein the main step of the first sterilizing is performed in a sterilization chamber.

3. The method of claim 1, wherein the main step of the first sterilizing comprises exposing the syringe barrel together with the needle adaptor cap assembled on the tip of the syringe barrel to a pressure of about 450 millibars to about 1000 millibars.

4. The method of claim 1, wherein in the main step of the first sterilizing, the ethylene oxide is provided in a concentration of about 400 milligrams per liter to about 800 milligrams per liter.

5. The method of claim 1, wherein the main step of the first sterilizing comprises flushing the syringe barrel together with the needle adaptor cap assembled on the tip of the syringe barrel with air, nitrogen or a combination thereof at a pressure of about 100 millibars or about 200 millibars to about 800 millibars or about 900 millibars after exposing the syringe barrel together with the needle adaptor cap to ethylene oxide.

6. The method of claim 1, wherein the first sterilizing comprises a pre-conditioning step of exposing the syringe barrel together with the needle adaptor cap assembled on the tip of the syringe barrel to ethylene oxide for about 12 hours to about 96 hours at a relative humidity of about 40% to about 100% and at a temperature of about 30° C. to about 60° C., wherein the pre-conditioning step of the first sterilizing is executed prior to the main step of the first sterilizing, and wherein the pre-conditioning step of the first sterilizing preferably is performed outside a sterilization chamber.

7. The method of claim 1, wherein the first sterilizing comprises a pre-conditioning step of exposing the syringe barrel together with the needle adaptor cap assembled on the tip of the syringe barrel to ethylene oxide for about 10 minutes to about 2 hours at a relative humidity of about 40% to about 100% and at a temperature of about 30° C. to about 60° C., wherein the pre-conditioning step of the first sterilizing is executed prior to the main step of the first sterilizing, and wherein the pre-conditioning step of the first sterilizing preferably is performed inside a sterilization chamber.

8. The method of claim 1, wherein the first sterilizing comprises an aeration step of exposing the syringe barrel together with the needle adaptor cap assembled on the tip of the syringe barrel to an air flow for about 12 hours to about 96 hours at a temperature of about 30° C. to about 60° C., and wherein the aeration step of the first sterilizing is executed after the main step of the first sterilizing.

9. The method of claim 1, wherein the main step of the second external surface sterilizing is performed in a sterilization chamber.

10. The method of claim 1, wherein the main step of the second external surface sterilizing comprises exposing the packaged syringe barrel together with the rubber stopper sealing the interior of the syringe barrel and the needle adaptor cap assembled on the tip of the syringe barrel to a pressure of about 450 millibars to about 1000 millibars.

11. The method of claim 1, wherein in the main step of the second external surface sterilizing the ethylene oxide is provided in a concentration of about 400 milligrams per liter to about 800 milligrams per liter.

12. The method of claim 1, wherein the main step of the second external surface sterilizing comprises flushing the packaged syringe barrel together with the rubber stopper sealing the interior of the syringe barrel and the needle adaptor cap assembled on the tip of the syringe barrel with air, nitrogen or a combination thereof at a pressure of about 100 millibars or about 200 millibars to about 800 millibars or about 900 millibars after exposing the syringe barrel together with the rubber stopper sealing the interior of the syringe barrel and the needle adaptor cap assembled on the tip of the syringe barrel to ethylene oxide.

13. The method of claim 1, wherein the second external surface sterilizing comprises a pre-conditioning step of exposing the packaged syringe barrel together with the rubber stopper sealing the interior of the syringe barrel and the needle adaptor cap assembled on the tip of the syringe barrel to ethylene oxide for about 12 hours to about 96 hours at a relative humidity of about 40% to about 100% and at a temperature of about 25° C. to about 45° C., wherein the pre-conditioning step of the second external surface sterilizing is executed prior to the main step of the second external surface sterilizing, and wherein the pre-conditioning step of the second external surface sterilizing preferably is performed outside a sterilization chamber.

14. The method of claim 1, wherein the second external surface sterilizing comprises a pre-conditioning step of exposing the packaged syringe barrel together with the rubber stopper sealing the interior of the syringe barrel and the needle adaptor cap assembled on the tip of the syringe barrel to ethylene oxide for about 10 minutes to about 2 hours at a relative humidity of about 40% to about 100% and at a temperature of about 25° C. to about 45° C., wherein the pre-conditioning step of the second external surface sterilizing is executed prior to the main step of the second external surface sterilizing, and wherein the pre-conditioning step of the second external surface sterilizing preferably is performed inside a sterilization chamber.

15. The method of claim 1, wherein the second external surface sterilizing comprises an aeration step of exposing the packaged syringe barrel together with the rubber stopper sealing the interior of the syringe barrel and the needle adaptor cap assembled on the tip of the syringe barrel to an air flow for about 12 hours to about 96 hours at a temperature of about 25° C. to about 45° C., and wherein the aeration step of the second external surface sterilizing is executed after the main step of the second external surface sterilizing.

16. The method of claim 1, wherein the filling of the drug substance into the interior of the syringe barrel and the sealing of the open end of the syringe barrel are performed in a cleanroom.

17. The method of claim 16, wherein the second external surface sterilizing is performed outside the cleanroom.

18. The method of claim 1, wherein, after the sealing of the open end of the syringe barrel, an auxiliary component is mounted to the syringe barrel.

* * * * *